(12) United States Patent
Mogensen et al.

(10) Patent No.: US 6,830,562 B2
(45) Date of Patent: Dec. 14, 2004

(54) INJECTOR DEVICE FOR PLACING A SUBCUTANEOUS INFUSION SET

(75) Inventors: Lasse Wesseltoft Mogensen, Søborg (DK); Magnus Walter Göransson, Malmö (SE); Grete Kornerup, Haslev (DK)

(73) Assignee: Unomedical A/S (DK)

( * ) Notice: Subject to any disclaimer, the term of this patent is extended or adjusted under 35 U.S.C. 154(b) by 0 days.

(21) Appl. No.: 09/995,237

(22) Filed: Nov. 26, 2001

(65) Prior Publication Data

US 2003/0060781 A1 Mar. 27, 2003

Related U.S. Application Data

(63) Continuation-in-part of application No. 09/967,400, filed on Sep. 28, 2001, now abandoned.

(30) Foreign Application Priority Data

Sep. 27, 2001 (DK) ........................ 2001 01411

(51) Int. Cl.⁷ ............................................. A61M 5/178
(52) U.S. Cl. ........................... 604/164.12; 604/164.01; 604/164.18; 604/136
(58) Field of Search ................................ 604/156, 157, 604/134–136, 93.01, 117, 158, 162, 164.01, 164.06, 164.08–164.12, 167.01–167.04, 167.06, 187, 192, 181, 199, 218, 220, 240–243, 264, 523, 272–274, 288.01–288.04, 905; 128/DIG. 26

(56) References Cited

U.S. PATENT DOCUMENTS

| | | | |
|---|---|---|---|
| 4,530,695 A | | 7/1985 | Phillips et al. |
| 4,755,173 A | * | 7/1988 | Konopka et al. ...... 604/167.02 |
| 4,817,603 A | | 4/1989 | Turner et al. |
| RE32,922 E | | 5/1989 | Levin et al. |
| 5,141,496 A | | 8/1992 | Dalto et al. |
| 5,147,375 A | | 9/1992 | Sullivan et al. |
| 5,176,662 A | * | 1/1993 | Bartholomew et al. ..... 604/513 |
| 5,248,301 A | * | 9/1993 | Koenig et al. ......... 604/288.02 |
| 5,257,980 A | * | 11/1993 | Van Antwerp et al. ..... 604/506 |
| 5,269,799 A | | 12/1993 | Daniel |
| 5,300,030 A | | 4/1994 | Crossman et al. |
| 5,350,392 A | | 9/1994 | Purcell et al. |
| 5,391,151 A | | 2/1995 | Wilmot |
| 5,540,709 A | | 7/1996 | Ramel |
| 5,545,152 A | * | 8/1996 | Funderburk et al. ......... 604/535 |
| 5,584,813 A | | 12/1996 | Livingston et al. ......... 604/177 |
| 5,591,188 A | | 1/1997 | Waisman |
| 5,599,315 A | | 2/1997 | McPhee |
| 5,665,071 A | | 9/1997 | Wyrick |
| 5,681,323 A | | 10/1997 | Arick |
| 5,741,288 A | | 4/1998 | Rife |
| 5,851,197 A | | 12/1998 | Marano et al. |
| 5,968,011 A | * | 10/1999 | Larsen et al. .......... 604/288.02 |
| 6,017,328 A | | 1/2000 | Fischell et al. ............. 604/180 |
| 6,056,718 A | * | 5/2000 | Funderburk et al. ..... 604/93.01 |
| 6,090,068 A | * | 7/2000 | Chanut .................... 604/93.01 |
| 6,093,172 A | | 7/2000 | Funderburk et al. |
| 6,099,503 A | | 8/2000 | Stradella |
| 6,293,925 B1 | * | 9/2001 | Safabash et al. ............. 604/136 |
| 6,293,926 B1 | | 9/2001 | Safabash et al. |
| 6,355,021 B1 | * | 3/2002 | Nielsen et al. .............. 604/263 |

FOREIGN PATENT DOCUMENTS

| | | | |
|---|---|---|---|
| WO | WO 89/05392 | * 6/1989 | |
| WO | WO 98/58693 | 12/1998 | ............ A61M/5/00 |
| WO | WO 99/33504 | 7/1999 | ............ A61M/5/20 |

* cited by examiner

Primary Examiner—Michael J. Hayes
Assistant Examiner—Cris L. Ridriguez
(74) Attorney, Agent, or Firm—Brinks Hofer Gilson & Lione

(57) ABSTRACT

An injector device has a plunger with a medical needle essentially non-detachably secured thereto, preferably a solid needle incapable of delivering a fluid, and is adapted for the quick and easy transcutaneous placement through the skin of a patient of the cannula of a subcutaneous infusion set, the insertion needle extending through the infusion set and protruding from the end of the cannula.

43 Claims, 10 Drawing Sheets

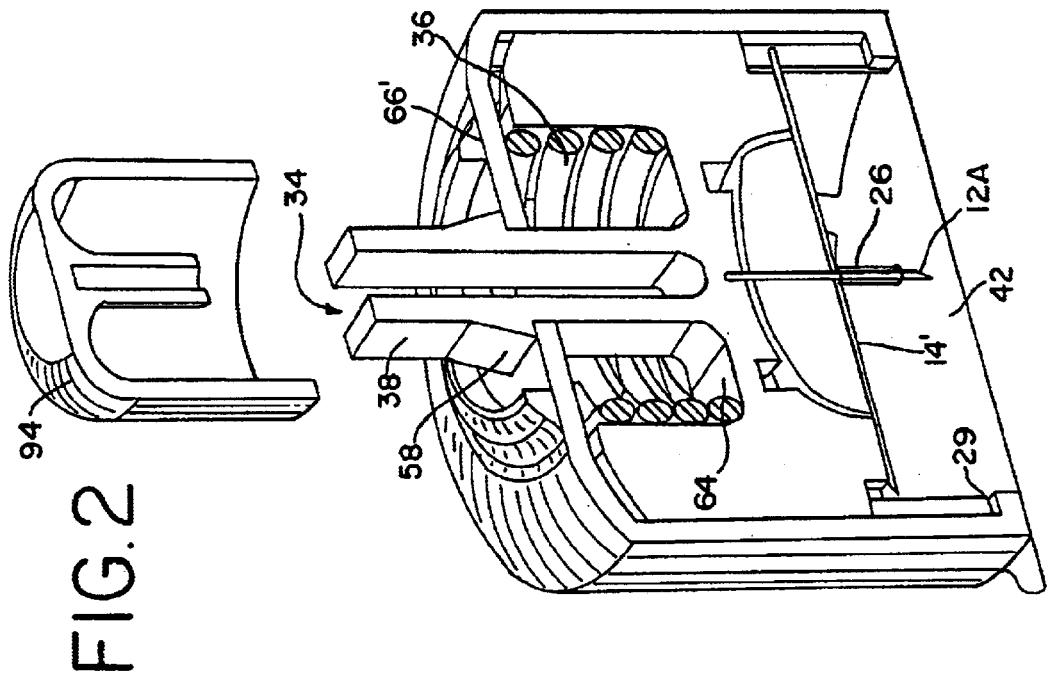
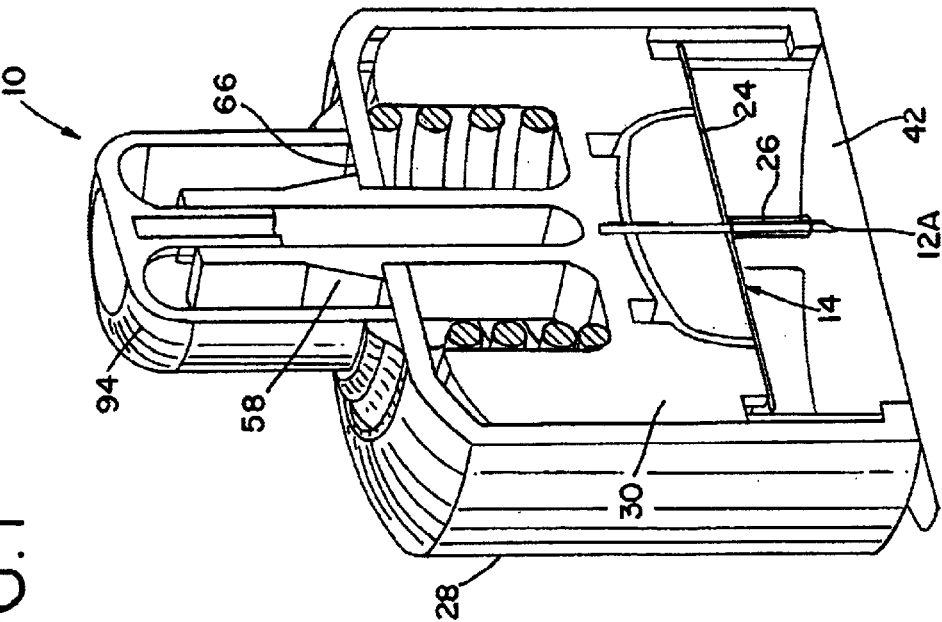

US 6,830,562 B2

INJECTOR DEVICE FOR PLACING A SUBCUTANEOUS INFUSION SET

This application is a continuation-in-part of 09/967,400 filed Sep. 28, 2001 now abandoned.

BACKGROUND OF THE INVENTION

This invention relates generally to an improved injector device for the placement of a subcutaneous infusion set on a patient. Examples of injector devices for the placement of a subcutaneous infusion set are disclosed in U.S. Pat. Nos. 6,093,172, 5,851,197 and WO 99/33504, incorporated by reference herein.

Medical needles are widely used in the course of patient treatment, particularly for delivery of selected medications. In one form, hollow hypodermic needles are employed for transcutaneous delivery of the medication from a syringe or the like, see U.S. Pat. No. 5,665,071. In another, as shown in U.S. Pat. No. 5,591,188 incorporated herein by reference, an insertion needle used in conjunction with an injector device is employed for transcutaneous placement of a soft and relatively flexible tubular cannula, followed by removal of the insertion needle and subsequent infusion of medical fluid to the patient through the cannula.

It is often necessary for a patient to transcutaneously place the medical needle himself. For example, diabetic patients frequently place a subcutaneous infusion set with a cannula for subsequent programmable delivery of insulin by means of a medication infusion pump. Such subcutaneous infusion sets are disclosed, for example, in U.S. Pat. Nos. 4,755,173, 5,176,662, 5,257,980 and WO 98/58693 which are incorporated by reference herein.

Some patients are reluctant or hesitant to pierce their own skin with a medical needle, and thus encounter difficulties in correct needle placement for proper administration of the medication. Such difficulties can be attributable to insufficient manual skill to achieve proper needle placement or alternately to anxiety associated with anticipated discomfort as the needle pierces the skin. This problem can be especially significant with medications delivered via a subcutaneous infusion set, since incorrect placement can cause kinking of the cannula and resultant obstruction of medication flow to the patient Cannula kinking can be due to infusion set placement at an incorrect angle relative to the patient's skin, and/or needle placement with an incorrect force and speed of insertion.

The present invention is aimed at providing an improved injector device, which may allow for a shortening of the total time required for the placement of an infusion set. The present invention also aims at providing an improved spring-type drive for urging a plunger within a housing to an advanced position.

SUMMARY OF THE INVENTION

In accordance with the invention, an injector device has a plunger with a medical needle, preferably a solid needle incapable of delivering a fluid, and is adapted for the quick and easy transcutaneous placement through the skin of a patient of the cannula of a subcutaneous infusion set, the insertion needle extending through the infusion set and protruding from the end of the cannula. The injector device is designed to place the cannula with the insertion needle extending therethrough with a controlled force and speed of insertion to ensure proper needle placement with minimal patient discomfort. The injector device may also allow placement of the insertion needle through the skin at a selected insertion angle.

Preferably, the injector device is provided to the patient as a sterile sealed, single use assembly including a subcutaneous infusion set with a housing already mounted on the insertion needle of the injector device, thereby reducing the number of components to be handled by the patient prior to the placement of the subcutaneous infusion set.

More particularly, the injector device comprises a device housing having an elongated bore formed therein and a plunger slidably received within the bore for movement between an advanced position and a retracted position, the plunger having substantially non-detachably secured thereto an insertion needle adapted to receive and support said cannula in a position with the cannula oriented for transcutaneous placement upon movement of the plunger with said needle from the retracted position to the advanced position. A drive urges the plunger with a controlled force and speed from the retracted position toward the advanced position to transcutaneously place said cannula of said subcutaneous infusion set received on said insertion needle. The insertion needle on the plunger is removable from said cannula while maintaining the transcutaneous placement of the cannula. By "substantially non-detachably" as used in the present application is meant a connection, which will remain stable under normal conditions of use to allow the needle to remain on the plunger when retracting the injector device from a patient's skin.

Preferably, the injector comprises a spring-loaded plunger having a head for receiving the infusion set in a position with the insertion needle projecting outwardly for transcutaneous placement through the skin of a patient. A front end of the housing is designed for pressed placement against the skin of a patient, at a selected needle insertion site, and in an orientation with the needle disposed at a correct or desired insertion angle. A trigger member is operable to release the plunger and thereby permit the drive spring to carry the infusion set toward the patient's skin with a controlled force and speed, resulting in proper transcutaneous placement of the insertion needle with minimal patient discomfort.

The invention also relates to a novel spring-type drive for urging the plunger of an injector device to the advanced position, preferably for transcutaneously placing a subcutaneous infusion set, wherein the drive comprises a number of individual, elongated flexible plastics members, preferably extending around a respective part of the periphery of the plunger, in the annular space between the plunger and a device housing. Each member is connected with the plunger and with the device housing. In the advanced position of the plunger, the plastics members are essentially plane and non-deformed. However, when moving the plunger to the retracted position, the plastics members are bend, setting up the required force that seeks to drive the plunger to an advanced position. The novel spring-type drive may also be implemented in injector devices of the type disclosed in U.S. Pat. Nos. 6,093,172, 5,851,197 and WO 99/33504 where the plunger head does not have an insertion needle mounted thereon for receiving an infusion set, but includes a recess adapted for receiving as well as supporting a subcutaneous infusion set.

BRIEF DESCRIPTION OF THE DRAWINGS

The accompanying drawings illustrate the invention.

FIG. 1 is a perspective schematic vertical cross-sectional view illustrating an injector device embodying the novel features of the invention, FIG. 2 is a schematic cross-sectional view of the injector device shown in FIG. 1, with the end cap removed.

DETAILED DESCRIPTION OF THE PREFERRED EMBODIMENTS

Figure 4:
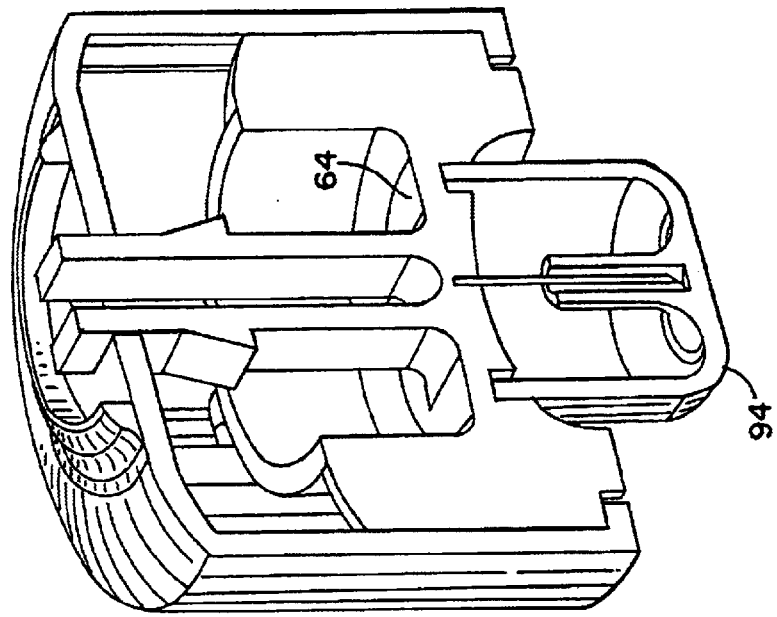
FIG. 4 is a view similar to FIG. 3 with end cap placed for protection of the protruding insertion needle.

An injector device shown schematically in FIG. 1 by the reference numeral 10 is provided for quick and easy placement of a subcutaneous infusion set 14, and may then be discarded safely. The infusion set 14 with a cannula 26 extending therefrom is shown schematically only.

The injector device 10 includes a plunger 30 having thereon a medical insertion needle 12 with a pointed end 12A. The plunger 30 is arranged for longitudinal sliding movement within a device housing 28 between a forward advanced position (FIGS. 3 and 4) and a rearward retracted position (FIGS. 1 and 2). The device housing 28 may have a circular, square or any desired cross-sectional shape. The device housing 28 and the plunger 30 are preferably formed of a plastics material.

The infusion set 14 is used to infuse medical fluids such as insulin to a patient, and generally includes a housing with an internal chamber (not shown) that receives medication via infusion tubing. An enlarged base 24 of the infusion set 14 is provided on the housing for stable affixation thereof to the skin of the patient. The infusion set has a protruding soft and flexible cannula 26, which communicates with the internal chamber, and a passage sealed by a sealing membrane extends through the housing opposite the cannula 26. The medical insertion needle 12 of the injector device 10 extends through the passage, into the internal chamber and through the cannula 26, when the infusion set 14 is mounted in position on the injector device. After transcutaneous placement of the cannula 26, the injector device 10 with the insertion needle 12 is retracted from the infusion set 14 to permit medication delivery through the cannula 26 to the patient.

Examples of subcutaneous infusion sets suitable for use with the injector device of the present invention, and in particular in conjunction with the insertion needle of the injector device, are shown and described in U.S. Pat. Nos. 4,755,173, 5,176,662 and 5,257,980, and in international patent application No. 98/58693, which are incorporated by reference herein. Such infusion sets generally include a hollow cannula part. The insertion needle shown in those publications may be obviated through the present invention. Alternatively, the injector device according to the invention may be used to transcutaneously place a cannula associated with other types of infusion sets.

The invention provides a ready to use injector device, which may be molded from a suitable plastics material. An injector device assembly including the injector device and a subcutaneous infusion set will effectively simplify the placement of an infusion set as the assembly, as delivered from the factory, provides an infusion set already mounted on the insertion needle 12. The time required for the placement of an infusion set is reduced.

The injector device 10 includes a trigger-type actuator mechanism for transcutaneous placement, with a controlled speed and force, of the insertion needle 12 which is secured to the plunger 30, with the insertion needle 12 oriented at a desired angular position relative to the skin of the patient in principally the manner as shown in international patent application No. 99/33504 incorporated herein by reference.

The plunger 30 has a recessed head 32 (FIG. 3) at a lower or forward end thereof shaped for receiving the housing of the subcutaneous infusion set 14. Centrally in the recess, the head 32 is provided with the metal insertion needle 12, which is securely connected thereto. Preferably, the insertion needle 12 is connected to the plunger in the process of molding the plunger 30, or the insertion needle 12 may be press-fit in the plunger 30. The recess in the plunger head 32 need not provide support for the infusion set 14 in the sense of providing resistance to removal of the infusion set 14. Such support is preferably provided solely by the frictional engagement of the insertion needle 12 with the cannula 26 or preferably with the sealing membrane within the internal chamber of the infusion set 14. A rear end of the plunger 30 has a trigger-type actuator assembly 34 cooperating with the rear end of the device housing 28, and includes a stem, which is longitudinally split to define a pair of trigger arms 38 which have out-turned trigger fingers 58 on the sides thereof. The trigger actuator assembly 34 is adapted to hold the plunger 30 in a retracted position, against the force of a compressed helical drive spring 36. The trigger arms 38 of the actuator assembly 34 are adapted for fingertip depression to release the plunger 30 for spring-loaded travel toward the advanced position, and for corresponding transcutaneous placement of the insertion needle 12, and of the cannula 26 travelling therewith, through the patient's skin.

Figure 3:
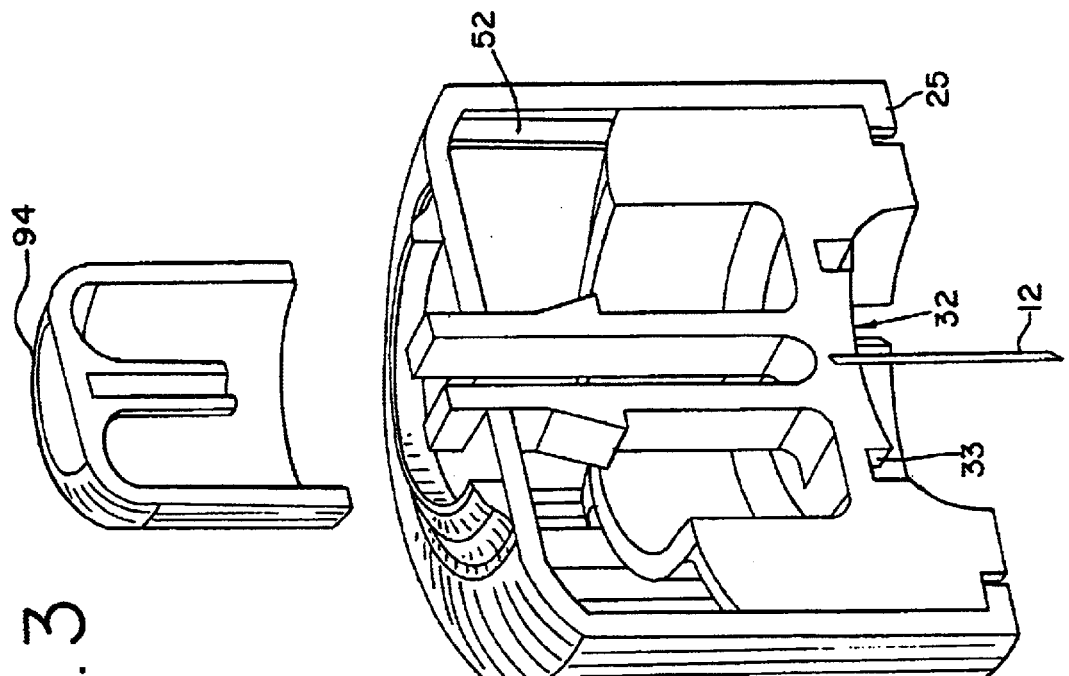
FIG. 3 is a schematic cross-sectional view of the injector device of FIG. 1, with the plunger in the advanced position and after placement of the subcutaneous infusion set.
Figure 5:
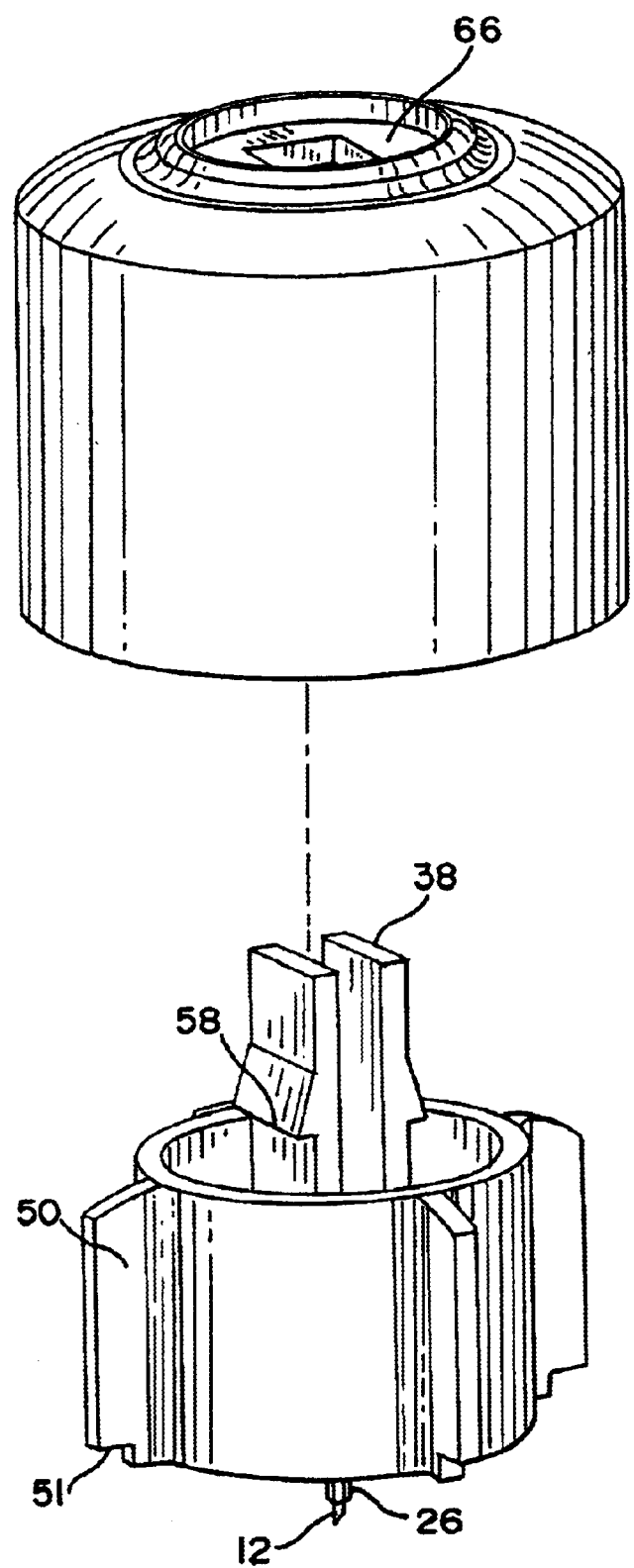
FIG. 5 is an exploded perspective view illustrating the plunger and housing parts of the injector device.
Figure 6:
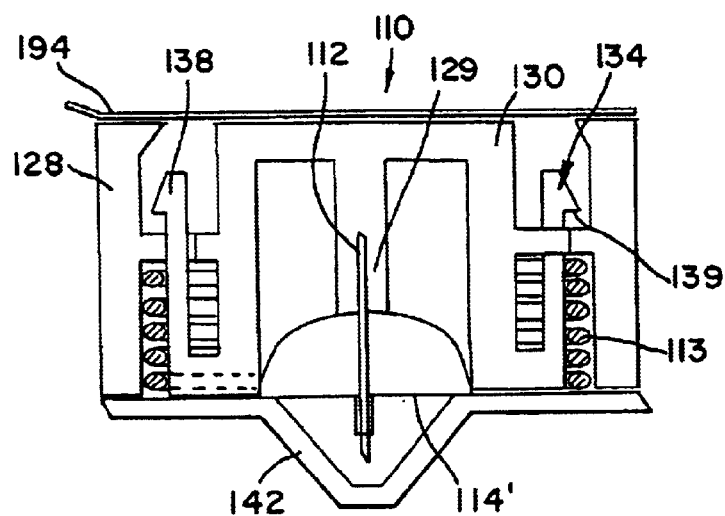
FIG. 6 is a highly schematic vertical partly cross-sectional view illustrating an injector device according to a second embodiment of the invention, prior to use.

FIGS. 1–5 illustrate construction details of the injector device housing 28, wherein the lower or nose end thereof defines a flat and generally planar peripheral surface 25 for placement against the skin of a patient with a longitudinal axis of the device housing 28 oriented generally perpendicular to the patient's skin. The hollow bore of the device housing 28 has a size and shape for reception of the infusion set 14, with the insertion needle 12 extending through the cannula 26 and extending together with the cannula 26 in a direction for placement on a patient. A releasable cover sheet 42 (FIGS. 1 and 2) is preferably secured to the device housing 28 at the nose end thereof to indicate the sterility of the infusion set 14. The device housing 28 may also include a narrow slot (not shown) extending parallel with the insertion needle 12 to accommodate slide-fit reception of a coupling element projecting laterally from the infusion set housing for coupling of the infusion set with a pump (not shown), and longitudinally extending track slots 52 (FIG. 3). The plunger 30 includes ribs 50 for guided reception within the track slots 52 formed in the device housing 28 to control the movement of the plunger 30 between the advanced position and the retracted position. The plunger 30 ribs 50 define a surface 51 near the head 32 adapted to cooperate with a peripheral inner edge 29 at the nose end of the device housing 28 to limit movement of the plunger, thereby defining the advanced position of the plunger 30.

Thus, the forward or nose end of the device housing 28 accommodates movement of the subcutaneous infusion set 14 between the retracted position disposed substantially at the rearward most end of the device housing 28, and the advanced position.

As will be understood, the trigger-type actuator assembly 34 generally functions to releasably retain the plunger 30 in the retracted and cocked position, ready for rapid and spring-loaded actuation upon depression of the trigger arms 38 to place the infusion set 14 on the patient. More particularly, the trigger assembly 34 is initially locked against a shoulder 66 formed on the device housing 28 by means of the trigger fingers 58. The drive spring 36 comprises a coil spring positioned about the stem on the plunger 30 and reacts between a rearward face 64 of the plunger head 32, and an internal shoulder 66' on the device housing 28. The drive spring 36 normally biases the plunger 30 toward the advanced position. During manufacture of the injector device assembly, the infusion set 14 is seated in the recess formed in the plunger head 32, either before or after the plunger 30 is moved to the retracted position. In this retracted plunger position, the drive spring 36 is retained in a compressed and cocked condition, with the cannula 26 of the infusion set 14 being received on the insertion needle 12. The releasable cover sheet 42 is then applied to the device housing 28 at the nose end thereof.

In use of the injector device 10 with the infusion set 14, the cover sheet 42 is first removed and the injector device 10 is placed firmly against the patient's skin, with the infusion set 14 supported in the proper orientation and at a predetermined distance from the skin. A cap 94, which prevents accidental projection of the infusion set 14 by preventing access to the trigger arms 38, is removed. Simple depression of the arms 38 releases the cocked plunger 30 for spring-loaded travel rapidly albeit with a controlled speed and force of insertion, to ensure penetration of the patient's skin with minimal discomfort, and in a manner which properly places the insertion needle and cannula 26.

Following placement of the infusion set 14 the injector device with insertion needle 12 is withdrawn quickly and easily from the cannula. Thereafter, the injector device can be discarded and the infusion set 14 can be used in a normal manner to deliver a selected medication through the infusion tubing and cannula 26 to the patient. As shown in FIG. 4, the safety cap 94 may conveniently be adapted to cooperate with an annular recess 33 formed in the head 32 of the plunger 30 for providing protection against the needle 12.

It is noted that the removable cap 94, when sealed to the device housing 28 at the end opposite the plunger head, together with the cover sheet 42 enable the injector device 10 together with the infusion set 14 mounted on the insertion needle 12 to be sterilised in a conventional sterilisation process using e.g. ethylene oxide, where the sterilising agent flows through the membrane formed by the cover sheet 42.

An alternative embodiment of the invention is shown schematically in FIGS. 6–12, wherein components corresponding in function to those described previously with respect to FIGS. 1–5 are identified by common reference numerals increased by 100. FIGS. 6–12 serve the purpose of explaining the principles involved in that embodiment, and the figures show schematic, partial cross-sectional views of the injector device.

FIGS. 6–12 show a modified injector device 110 constructed from a reduced number of parts and including an alternative drive mechanism for advancing the plunger. The modified injector device 110 comprises a generally cylindrical hollow device housing 128, a plunger 130 and a trigger-type actuator 134 formed integrally with the plunger 130. A cover 194, preferably a flexible membrane, covers the top of the injector device 110 and a further cover 142 covers the bottom end of the injector device 110.

The plunger 130 has a generally cylindrical form with a head 132 and a central pin 129 including a metal insertion needle 112 secured thereto in a molding process, by press-fit, or by any other method providing a suitable resistance to loss of the insertion needle during use of the device. The pin 129 stops at a distance from a pair of outwardly turned legs 138' at the head 132, to accommodate for the housing of the infusion set 14 in the head 132 of the plunger 130. The insertion needle 112 extends through the infusion set 114 in a similar manner as described with reference to FIGS. 1–6. An infusion set tubing 113 connected to the infusion set 114 is wound up in the lower part of an annular space 115 between the device housing 128 and the plunger 130.

Figure 9:
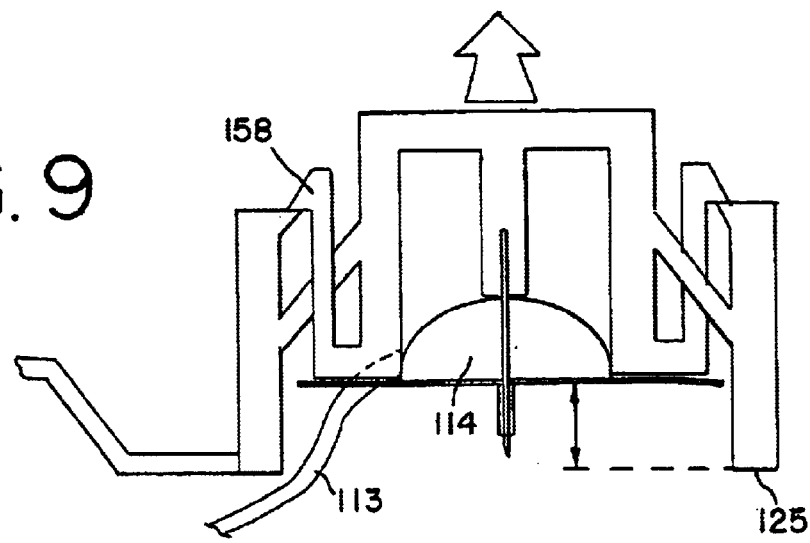
FIG. 9 is a view similar to FIG. 6 with the plunger being retracted and the injector device made ready for transcutaneous placement of the infusion set.
Figure 10:
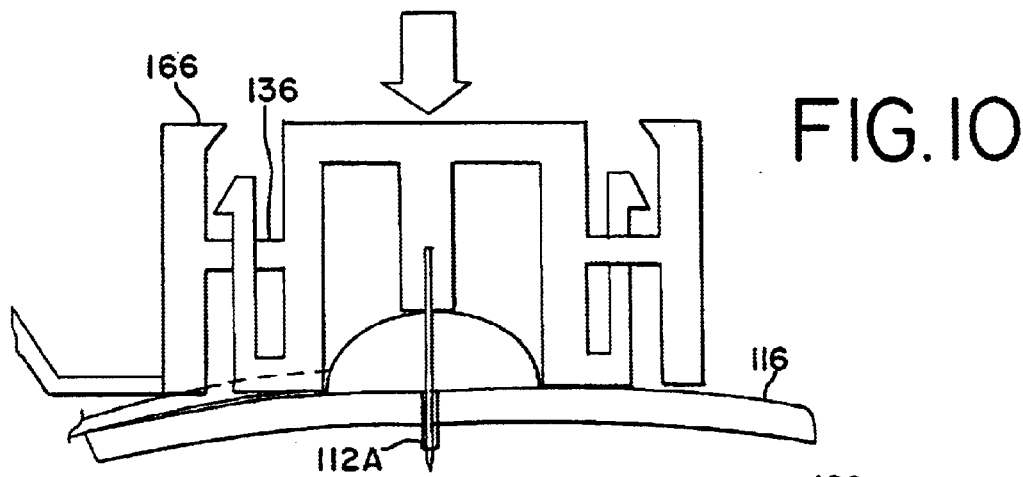
FIG. 10 is a view similar to FIG. 6, with the infusion set being placed on a patient.
Figure 11:
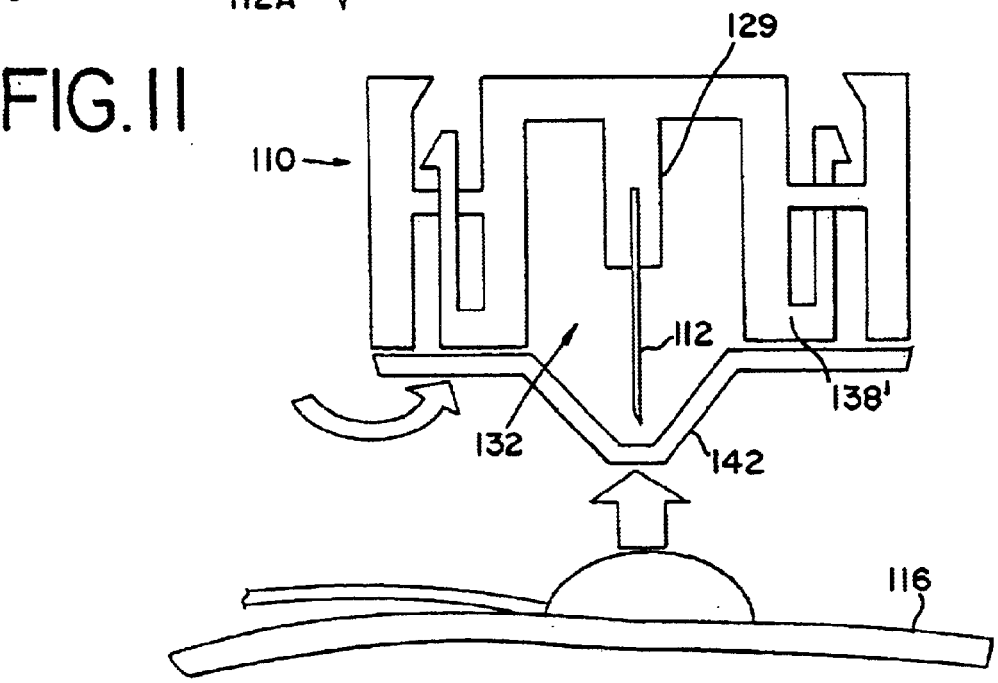
FIG. 11 is a view similar to FIG. 6, with the injection device being removed from the infusion set placed on the patient.
Figure 12:
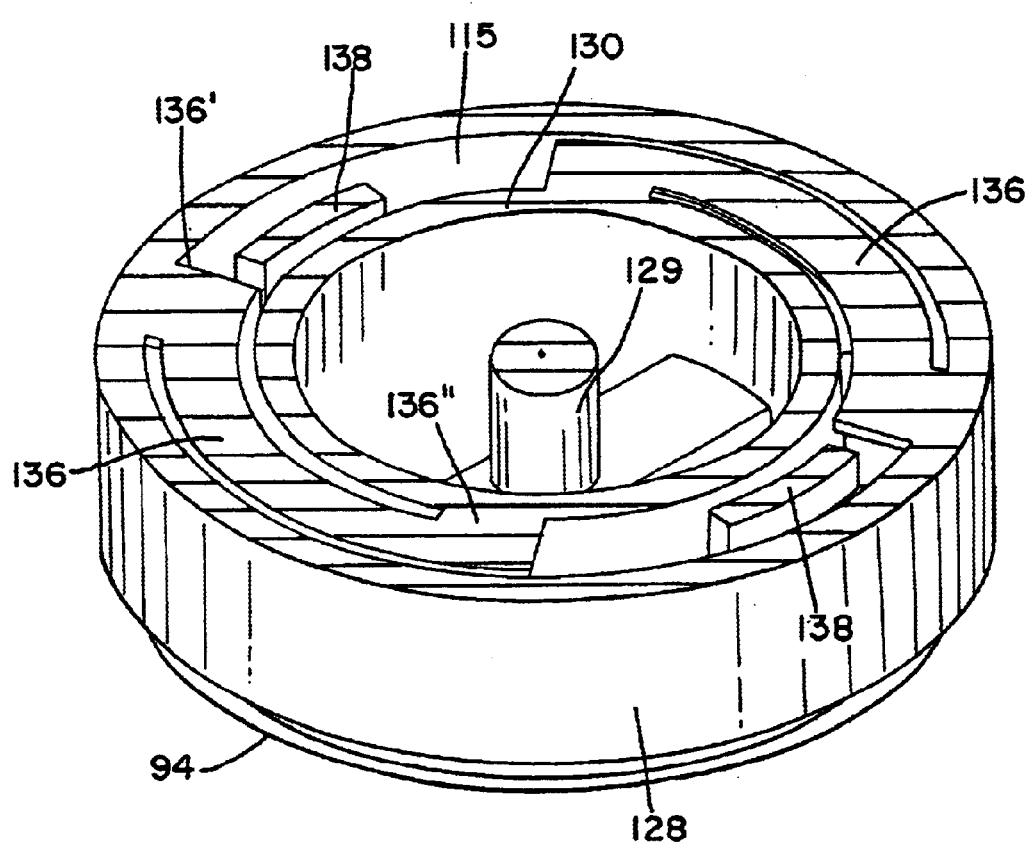
FIG. 12 is a horizontal perspective, cross-sectional view of the device shown in FIGS. 6–11, showing the spring-type drive with the plunger in the advanced position.

More specifically, the device housing 128 again has a forward or nose end defining a flat and generally planar surface 125 for firm placement against the skin of a patient. The plunger 130 additionally includes a pair of resilient trigger arms 138 which are connected with the pair of outwardly turned legs 138' and which have out-turned trigger fingers 158 at the sides thereof. The trigger arms 138 are adapted and sized for partial radial compression toward each other as they ride within the device housing when the plunger 130 is displaced from the advanced position (FIG. 6) to the retracted position (FIG. 9). As the retracted position is reached, the trigger arms 138 are spring-loaded by the resiliency to move first inwardly and then outwardly whereby the trigger fingers engage the upper surface of a shoulder 166 of the device housing 128. In this position the trigger fingers 158 retain the plunger 130 in the retracted position.

A drive spring 136 is mounted within the device housing 128 to drive the plunger towards the nose of the device housing in the retracted position of the plunger 130, upon release of the trigger arms 138. The drive spring 136 is formed integrally with the device housing 128 and the plunger 130 in a molding process and may conveniently be formed of the same plastics material as the plunger 130 and the device housing 128. The spring is shown in closer details in FIG. 12. The spring 136 essentially comprises a number of elongated plastics strips 136, each extending around a respective part of the periphery of the plunger 130, in the annular space 115 between the plunger 130 and the device housing 128. The drawing show an embodiment incorporating two such strips that each extends around about one fourth of the periphery of the plunger 130. Each strip 136 is integrally connected at one end 136" with the plunger 130 and with the device housing 128 at the other end 136'. In the advanced position of the plunger shown in FIGS. 6–8 and 10–12, the strips 136 are preferably essentially plane and non-deformed, However, when moving the plunger 130 to the retracted position shown in FIG. 9, the strips 136 of the spring are bend, setting up the required force that seeks to drive the plunger 130 towards the nose of the device housing 128. It is noted that this process normally gives rise to a rotational movement of the plunger 130 about its central axis, which is coincident with the insertion needle 112.

Figure 7:
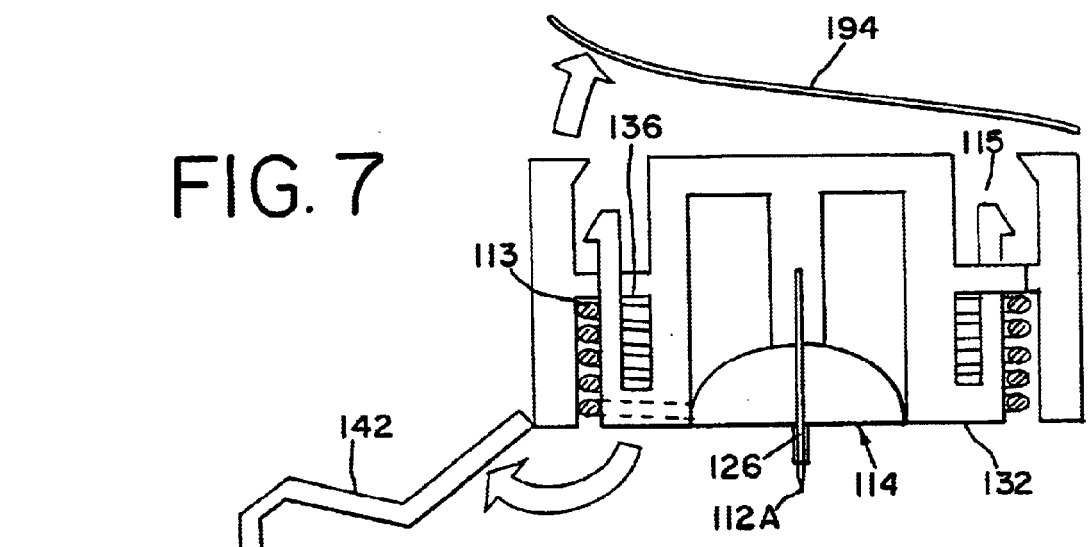
FIG. 7 is a view similar to FIG. 6, illustrating the injector device being made ready for use.
Figure 8:
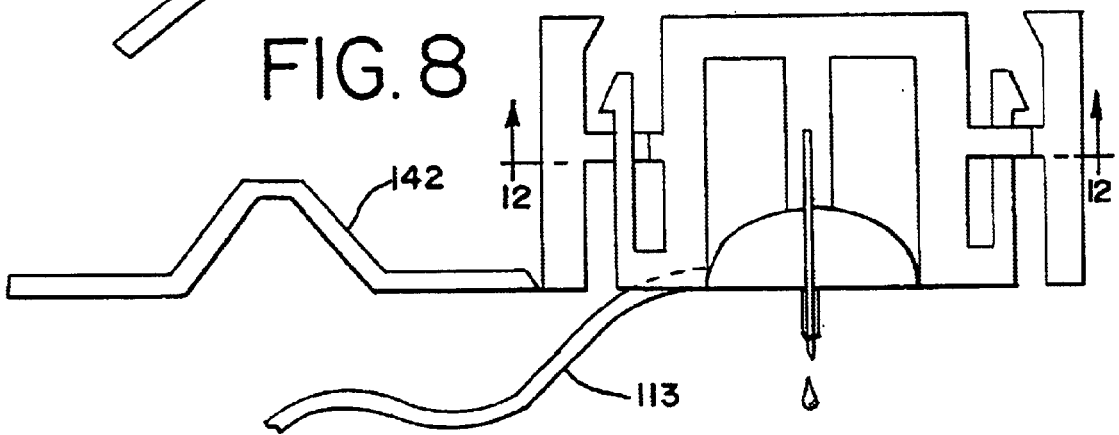
FIG. 8 is a view similar to FIG. 6 of the infusion device being primed.

Operation of the injector device assembly shown in FIGS. 6–12 is as follows. Since the injector device is preferably delivered to the patient in an uncocked state to simplify the process of manufacture, the plunger 130 must first be moved to the retracted position. To allow for retraction of the plunger 130, the upper cover 194, which spans across the device housing 128, and the lower cover 142 are first removed, as shown in FIG. 7. The lower cover 142 may be hingedly connected to the device housing 128. In this process, the infusion set 114 is exposed with the pointed end 112A of the insertion needle 112 projecting from the end of the soft flexible cannula 126. The infusion set tubing 113 is then connected to a suitable pump, and the infusion set 114 is primed by allowing medication to exit through the narrow annular space between the cannula 126 and the insertion needle 112. The injector device 110 is then cocked by displacing the plunger 130 with respect to the device housing 120 as illustrated by the arrow in FIG. 9, until the fingers 158 engage the upper shoulder 166 of the device housing 120, indicating that the injector device is now ready for use. A release sheet 114' is then removed exposing an adhesive material on the bottom side of the infusion housing 114, and the patient or the nursing personnel then places the injector device on the patient's skin. The plunger 130 is released by application of an inwardly directed manual force on the arms 138 to transcutaneously place the insertion needle 112 and the cannula 126. The injector device 110 is then removed, leaving the infusion set 114 on the patient's skin, illustrated by reference numeral 116, and the bottom cover 142 is then repositioned at the original place shown in FIG. 11 for protection of the insertion needle 112 which projects partially from the nose end of the device housing 128.

The removable upper cover 194 and the bottom cover 142, when sealed to the device housing 128, allow the injector device 110 together with the infusion set 14 mounted on the insertion needle 112 to be sterilised in a conventional sterilisation process using e.g. ethylene oxide, where the sterilising agent flows through a permeable membrane formed by one or both cover sheets 142, 194.

FIGS. 13–16 show a third embodiment of the invention wherein components corresponding in function to those described previously with respect to FIGS. 1–5 are identified by common reference numerals increased by 200. FIGS. 13–16 serve the purpose of explaining the principles involved in that embodiment, and the figures show schematic, partial cross-sectional views of an injector device 210. The injector device 210 is particularly suitable for the placement of a subcutaneous infusion set 214 at an acute angle relative to the skin of a patient.

Figure 13:
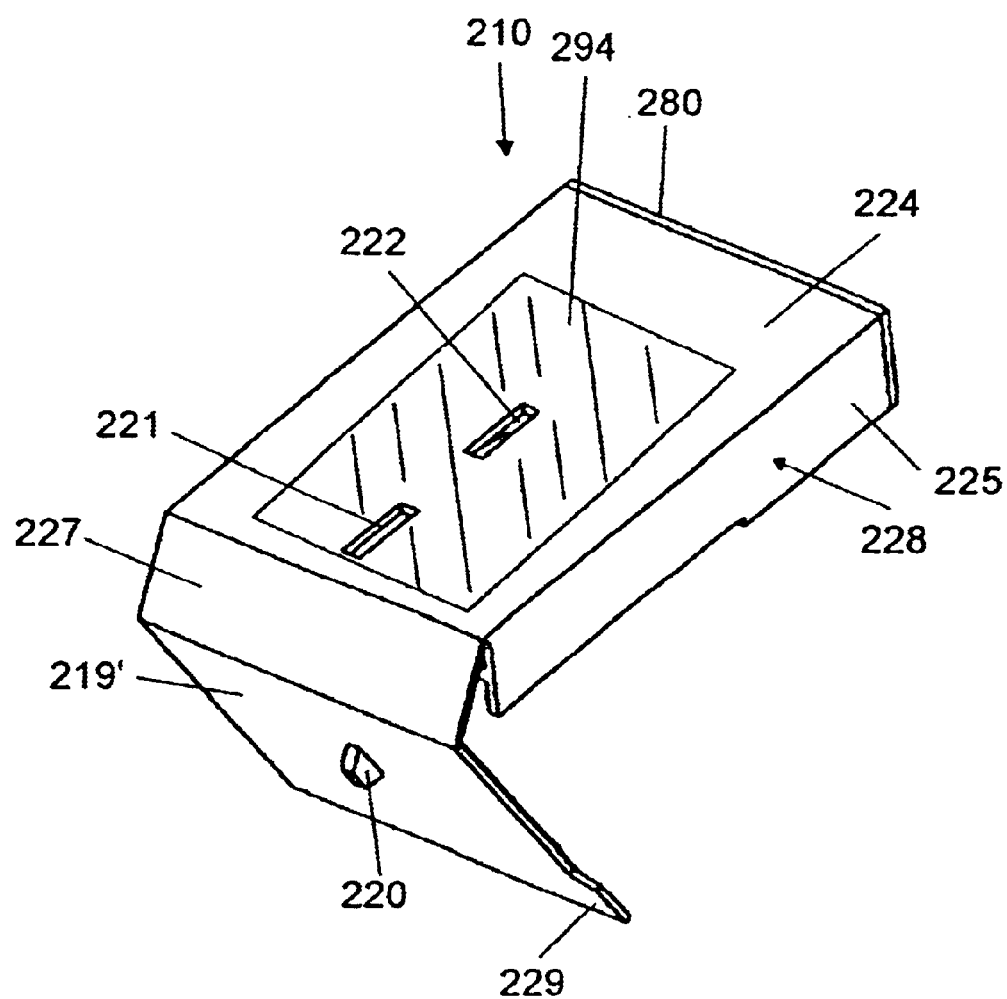
FIG. 13 is a perspective view illustrating an injector device according to a third embodiment of the invention, prior to use.
Figure 16:
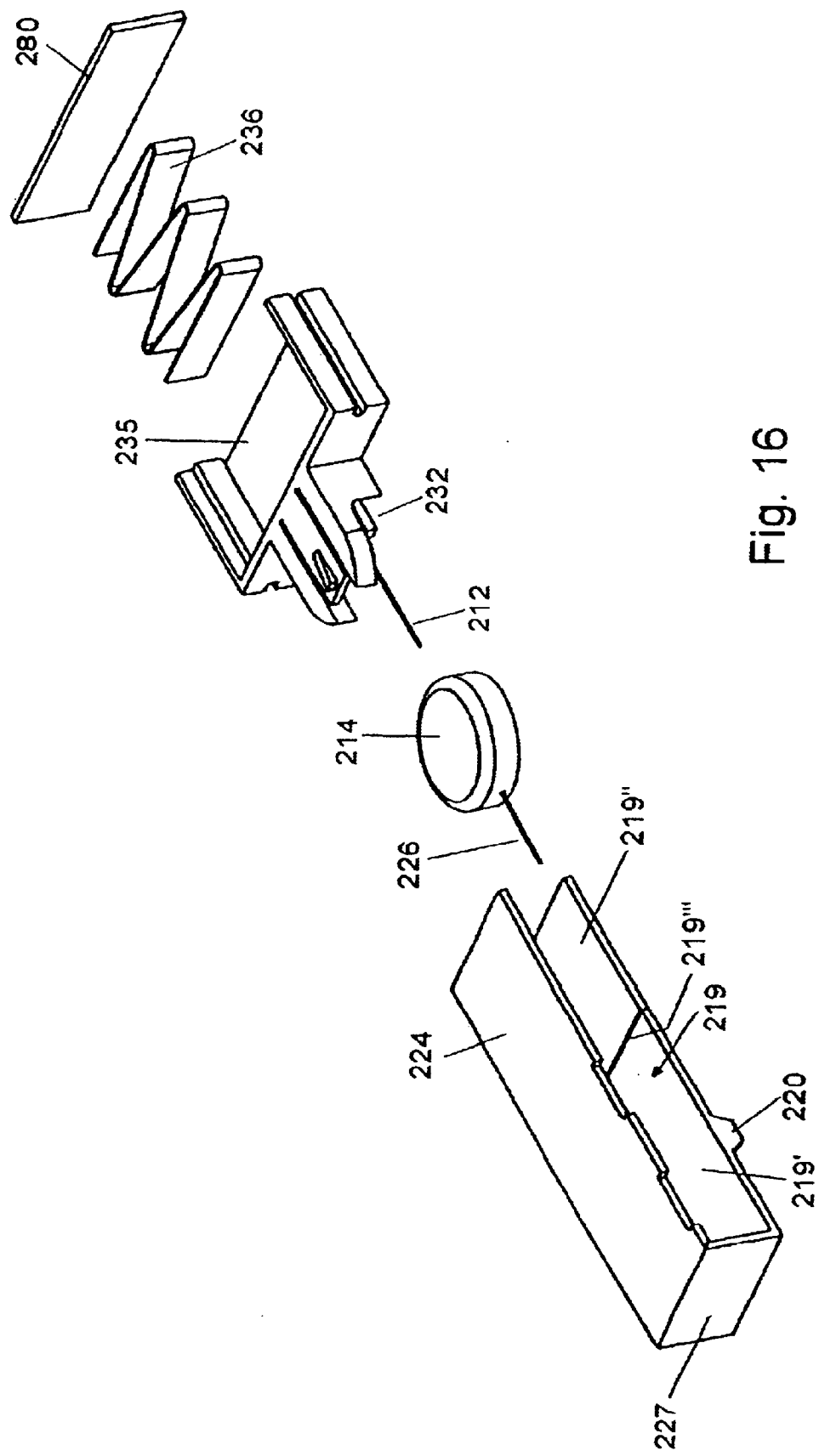

As best seen in FIG. 13, which shows the injector device in a semi-open state, the injector device 210 has a device housing 228 with a flattened box-like structure with parallel major walls 224, 219, the wall 219 including a frangible area 219''', see FIG. 16, allowing the wall 219 to be split by manually pulling flap 229 (FIG. 13), thereby forming two separate wall parts 219', 219" for a purpose that will be explained later. The housing 228 also includes a front wall 227 at the nose end of the injector device, and a rear wall 280, and opposed parallel side walls 225 frangibly connected to wall part 219'. The injector device 210 is presented to the consumer as a closed, box-shaped item, which may easily be provided with printed text as required.

Figure 14:
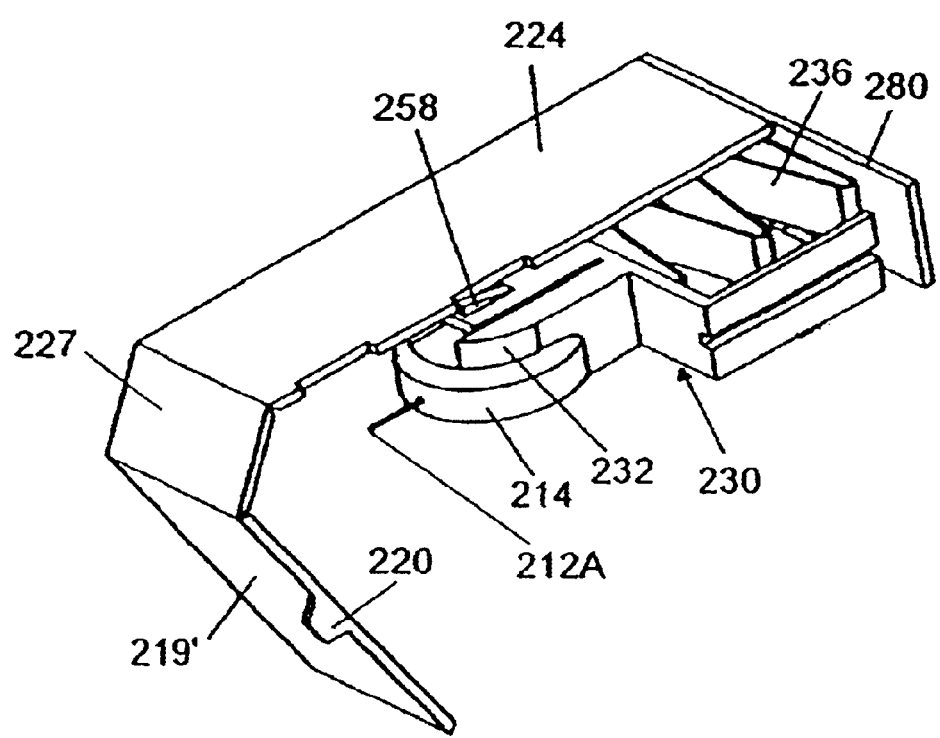
FIG. 14 is a perspective, partly cross-sectional view of the device of FIG. 13.

FIG. 14 shows the injector device in the same state shown in FIG. 13; however, a part of the walls 224, 227 and 219, as well as wall 225 have been omitted to show the interior of the injector device 210.

Figure 15:
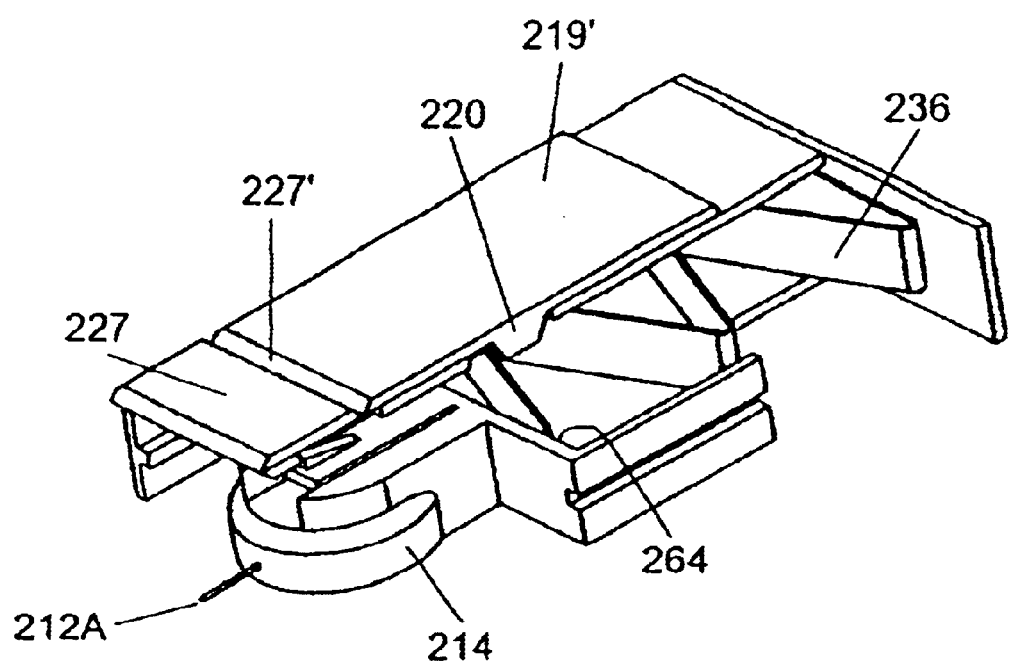
FIG. 15 is a view similar to FIG. 14, showing the plunger in the advanced position, and FIG. 16 a exploded perspective view illustrating the various parts of the injector device of FIGS. 13–15.

The injector device 210 comprises a plunger 230 mounted for longitudinal sliding movement within the box-shaped housing between a rearward retracted position (FIG. 14) and a forward advanced position (FIG. 15). The device housing 228 and the plunger 230 are preferably formed of a plastics material. The device housing 228 may alternatively be manufactured from a blank of rigid cardboard. The plunger 230 has a recessed head 232 (best seen in FIG. 16) at a forward end thereof shaped for receiving the housing of a subcutaneous infusion set 214. Centrally in the recess, the head 232 is provided with a projecting metal insertion needle 212, having a forward end 212A, securely connected thereto. The plunger 230 need not provide support for the infusion set as understood in the sense of providing resistance to removal of the infusion set. Such support may preferably be provided by the frictional engagement of the insertion needle 212 with the infusion set 214. A drive spring 236 positioned behind wall 280 reacts between a rearward faces 264 of the plunger head 232. The drive spring 236 normally biases the plunger 230 toward the advanced position. The front end of the plunger 230 has a trigger button 258 cooperating with the wall 224 of the device housing 228. In the retracted state of the plunger shown in FIG. 14, the trigger button 258 extends through an opening 222 formed in the upper wall 224 of the device housing 228 and aligned for reception of a release tab 220 on the wall 219', as will be explained.

The trigger button 258 may be adapted for fingertip depression to release the plunger 230 for spring-loaded travel toward the advanced position, and for corresponding transcutaneous placement of the insertion needle 212, and of the cannula 226 travelling therewith, through the patient's skin. Preferably, the button 258 is depressed by pivoting wall part 219' about line 227'. When the tab 220 formed on the external surface of wall part 219' is aligned with the slot 221, the trigger button 258 can be depressed to actuate the spring-locked plunger, by manually pressing down wall part 219".

Before opening the device housing 210, that is, before separating wall 219, 219' along frangible line 219''', the assembly is maintained under sterile conditions. A removable cover sheet 294 (FIG. 13) is sealed to wall 224 to cover opening 222. All other walls defining the closed housing 210 being sealed together, the cover sheet 294, when being permeable allows the injector device 210 together with the infusion set 214 mounted on the insertion needle 212 to be sterilised in a conventional sterilisation process using e.g. ethylene oxide, where the sterilising agent flows through the permeable membrane.

A variety of further modifications and improvements to the automatic injector device unit of the present invention will be apparent to persons skilled in the art. Accordingly, no limitation on the invention is intended by way of the foregoing description and accompanying drawings, except as set forth in the appended claims.

What is claimed is:

1. An injector device for transcutaneously placing a hollow cannula of a subcutaneous infusion set through the skin of a patient, comprising:
   a device housing having an elongated bore formed therein;
   a plunger slidably received within the bore movement between an advanced position and a retracted position, the plunger having an insertion needle substantially non-detachably secured thereto by a connection such that the insertion needle remains connected to the plunger is in the retracted position and the advanced position, said insertion needle for receiving and supporting the cannula of said subcutaneous infusion set in a position with the cannula oriented for transcutaneous placement upon movement of the plunger with said needle from the retracted position to the advanced position,
   a drive for urging the plunger with a controlled force and speed from the retracted position toward the advanced position to transcutaneous place said cannula of said subcutaneous infusion set received on said insertion needle,
   wherein said cannula is removable from the insertion needle secured to said plunger while maintaining the transucutaneous placement of the cannula.

2. The injector device of claim 1, wherein the device housing has a forward end defining generally planar surface for placement against the skin of a patient with the device housing in a predetermined orientation relative to the patient's skin.

3. The injector device of claim 2, wherein the infusion set comprises a tubing, said injector device including an annular space between said device housing and said plunger for accommodating said tubing.

4. The injector device of claim 1, wherein a forward end of said insertion needle opposite said plunger is substantially retracted within the bore of the device housing when the plunger is in the refracted position.

5. The injector device of claim 1, further including a trigger for actuating the drive.

6. The injector device at claim 5, wherein the trigger includes a trigger actuator for fingertip depression to actuate the drive for movement of the plunger from the retracted position to the advanced position.

7. The injector device of claim 5, wherein the trigger includes a lock for releasably locking the plunger in the retracted position.

8. The injector device of claim 1, wherein the device housing and the plunger include cooperatively engageable track means for guiding movement of the plunger between the advanced and retracted positions.

9. The injector device of claim 1, wherein the insertion needle is substantially incapable of delivering a fluid.

10. The injector device of claim 1, said cannula being soft and flexible.

11. The injection device of claim 1, wherein the drive comprises a spring for the plunger from the retracted position to the advanced position.

12. The injector device of claim 1, further including a cover at a forward end of the device housing for covering an infusion set received on said insertion needle and for covering said insertion needle subsequent to removal of said infusion set.

13. The injector device of claim 1, said device housing having a flat, box-shaped configuration.

14. The injector device of claim 1, further including a cover at a forward end of the device housing for covering an infusion set received on said insertion needle and for covering said insertion needle subsequent to removal of said infusion set.

15. An injector device for transcutaneously placing a hollow cannula of a subcutaneous infusion set through the skin of a patient, comprising:
   a device housing having an elongated bore formed therein,
   a plunger slidably received within the bore for movement between an advanced position and a retracted position, the plunger having substantially non-detachably secured thereto an insertion needle for receiving and supporting the cannula of said subcutaneous infusion set in a position with the cannula oriented for transcutaneous placement upon movement of the plunger with said needle from the retracted position to the advanced position, and
   a drive comprising a spring for urging the plunger with a controlled force and speed from the retracted position toward the advanced position to transcutaneously place said cannula of said subcutaneous infusion set received on said insertion needle,
   wherein the spring comprises a number of individual, elongated flexible plastic strips extending around a respective part of the periphery of the plunger, in a annular space between the plunger and the device housing, each strip being connected with the plunger and with the device housing: and
   wherein the insertion needle secured to said plunger is removable from said cannula while maintaining the transcutaneous placement of the cannula.

16. The injector device of claim 15, wherein the strips are integrally molded with said plunger and said device housing.

17. The injector device of claim 15, wherein each strip is connected at one end with the plunger and with the device housing at the other end, each strip being essentially plane and non-deformed in the advanced position of the plunger.

18. The injector device of claim 15, wherein the device housing has a forward end defining a generally planar surface for placement against the skin of a patient with the device housing in a predetermined orientation relative to the patient's skin.

19. The injector device of claim 15, wherein a forward end of said insertion needle opposite said plunger is substantially retracted within the bore of the device housing when the plunger is in the retracted position.

20. The injector device of claim 19, wherein the infusion set comprises a tubing, said injector device including an annular space between said device housing and said plunger for accommodating said tubing.

21. The injector device of claim 15, further including a trigger for actuating the drive.

22. The injector device of claim 21, wherein the trigger includes a trigger actuator for fingertip depression to actuate the drive for movement of the plunger from the retracted position to the advanced position.

23. The injector device of claim 21, wherein the trigger includes a lock for releasably locking the plunger in the retracted position.

24. The injector device of claim 15, wherein the insertion needle is substantially incapable of delivering a fluid.

25. The injector device of claim 15, said cannula being soft and flexible.

26. An injector device assembly, comprising:
   an infusion set including a housing and a hollow cannula
   a device housing having an elongated bore formed therein, a plunger slidably received within the bore for movement between an advanced position and a retracted position, the plunger having an insertion needle substantially non-detachably secured thereto by a connection such that the insertion needle remains connected to the plunger when the plunger is in the retracted position and the advanced position, said insertion needle carrying said cannula with the cannula oriented for transcutaneous placement upon movement of said plunger from the retracted position to the advanced position, a spring for urging said plunger toward the advanced position, and a trigger for releasably retaining the plunger in the retracted position, the trigger being operable to release the plunger for spring-loaded movement with a controlled force and speed toward the advanced position, wherein said cannula is removable from the insertion needle secured to said plunger while maintaining the transcutaneous placement of the cannula.

27. The injector device assembly of claim 26, wherein the device housing has a forward end defining a generally planar surface of placement against the skin of a patient with the device housing in a predetermined orientation relative to the patient's skin.

28. The injector device assembly of claim 26, wherein the device housing and the plunger include cooperatively engageable track means for guiding movement of the plunger between the advanced and retracted positions.

29. The injector device assembly of claim 26 wherein releasable cover members cover at least one end the device housing for assuring sterile conditions prior to use of the injector device assembly.

30. An injector device, comprising:

a molded device housing hiving an elongated bore formed therein, a molded plunger slidably received within the bore for movement between an advanced position and a retracted position, a drive for urging the plunger with a controlled force and speed from the retracted position toward the advanced position, wherein the drive comprises a number of individual, elongated flexible plastics members, each member being connected with the plunger and with the device housing.

31. The injector device claim 30, wherein each of said elongated flexible plastics members is connected at one end with the plunger and with the device housing at the other end, each member being essentially plane and non-deformed in the advanced position of the plunger.

32. The injector device of claim 26, wherein each member is formed as a strip, the device including at least two such strips, each strip extending around a respective part of the periphery of the plunger.

33. The injector device of claim 30, each of said members extending in an annular space between the plunger and the device housing.

34. The injector device of claim 30, used for transcutaneously placing an insertion needle of a subcutaneous infusion set through the skin of a patient, wherein the plunger includes a support structure for mated slide-fit reception and support of the infusion set in position with the insertion needle thereof oriented for transcutaneous placement upon movement of said plunger from the retracted position to the advanced position, wherein the support structure is removable from the infusion set while maintaining the transcutaneous placement of the insertion needle.

35. The injector device of claim 30, used for transcutaneously placing a subcutaneous infusion set through the skin of a patient by means of in insertion needle, wherein said insertion needle is substantially non-detachably secured to said plunger, and wherein said insertion needle receives and supports the cannula of the infusion set in position with the cannula oriented for transcutaneous placement upon movement of said plunger from the refracted position to the advanced position, wherein the insertion needle is removable from the infusion set while maintaining the transcutaneous placement of the cannula.

36. The injector device assembly of claim 30, wherein each of said members is integrally molded with said plunger and said housing device.

37. An injector device assembly, comprising:

an infusion set including a housing and a hollow cannula, a device housing having an elongated bore formed therein, a plunger slidably received within the bore for movement between an advanced position and a retracted position, the plunger having substantially non-detachably secured thereto an insertion needle carrying said cannula with the cannula oriented for transcutaneous placement upon movement of said plunger from retracted position to the advanced position;

a spring for urging said plunger toward the advanced position, the spring comprising a number of individual, elongated flexible plastics strips extending around a respective part of the periphery of the plunger, in an annular space between the plunger and the device housing, each strip being connected with the plunger and with the device housing; and a trigger for releasably retaining the plunger in the retracted position, the trigger being operable to release the plunger for spring-loaded movement with a controlled force and speed toward the advanced position, wherein the insertion needle secured to said plunger is removable from said cannula while maintaining the transcutaneous placement of the cannula.

38. The injector device assembly of claim 37, wherein the strips are integrally molded with said plunger and said device housing.

39. The injector device assembly of claim 37, wherein the device housing has a forward and defining a generally planar surface of placement against the skin of a patient with the device housing in a predetermined orientation relative to the patient's skin.

40. The injector device assembly of claim 37, wherein the device housing and the plunger include cooperatively engageable track means for guiding movement of the plunger between the advanced and retracted positions.

41. The injector device assembly of claim 37 wherein releasable cover members cover at least one end of the device housing for assuring sterile conditions prior to use of the injector device assembly.

42. An injector device for transcutaneously placing a hollow cannula of a subcutaneous infusion set through the skin of a patient, comprising:

a device housing having an elongated bore formed therein;

a plunger slidably received within the bore for movement between an advanced position and a retracted position, the plunger having substantially non-detachably secured thereto an insertion needle for receiving and supporting the cannula of said subcutaneous infusion set in a position with the cannula oriented for transcutaneous placement upon movement of the plunger with said needle from the retracted position to the advanced position, a drive for urging the plunger with a controlled force and speed from the retracted position toward the advanced position to transcutaneously place said cannula of said subcutaneous infusion set received on said insertion needle, wherein amid insertion needle is substantially non-detachably secured to said plunger in said retracted position and said advanced position; and wherein said cannula is removable from said insertion needle while maintaining the transcutaneous placement of the cannula.

43. An injector device assembly, comprising:

an infusion set including a housing and a hollow cannula;

a device housing having an elongated bore formed therein;

a plunger slideably received within the bore for movement between an advanced position and a retracted position, the plunger having substantially non-detachably secured thereto an insertion needle carrying said cannula with the cannula oriented for transcutaneous placement upon movement of said plunger from the retracted position to the advanced position;

a spring for urging said plunger toward the advanced position; and a trigger for releasably retaining the plunger in the retracted position, the trigger being operable to release the plunger for spring-loaded movement with a controlled force and speed toward the advanced position;

wherein said insertion needle is substantially non-detachably secured to said plunger in said retracted position and said advanced position; and wherein said cannula is removable from said insertion needle while maintaining the transcutaneous placement of the cannula.

* * * * *